United States Patent [19]

Carney et al.

[11] Patent Number: 5,352,664
[45] Date of Patent: Oct. 4, 1994

[54] THROMBIN DERIVED POLYPEPTIDES; COMPOSITIONS AND METHODS FOR USE

[75] Inventors: Darrell H. Carney, Galveston, Tex.; Kevin C. Glenn, St. Louis, Mo.

[73] Assignees: Board of Regents, The University of Texas System, Austin, Tex.; Monsanto Company, St. Louis, Mo.

[21] Appl. No.: 925,201

[22] Filed: Oct. 31, 1986

[51] Int. Cl.$^5$ .................. A61K 37/02; A61K 37/547; C07K 7/10; C12N 9/74
[52] U.S. Cl. .................................. 514/13; 530/326; 435/214; 424/94.64
[58] Field of Search ...................... 530/330, 327, 326; 514/2, 13, 14, 18; 435/214; 424/94.64

[56] References Cited

U.S. PATENT DOCUMENTS 4,427,651 1/1984 Stroetmann ............................ 424/45
4,606,337 8/1986 Zimmermann et al. ............. 604/358

OTHER PUBLICATIONS

Butkowski et al. (1977) JBC, 252:4942–4957, "Primary Structure of Human Prethrombin 2 and α–Thrombin".
Ruoslahti and Pierschbacher (1986), Cell, 44:517–518.
Carney et al. (1985), Cell, 42:470–488.
Carney et al. (1984), J. Cell. Biochem., 26:181–195.
Pierschbacher and Ruoslahti (1984), Proc. Natl. Acad. Sci. USA, 81:5985–5988.
Pierschbacher and Ruoslahti (1984), Nature, 309:30–33.
Degen et al. (1983), Biochem., 22:2087–2097.
Perdue et al. (1981), J. Biolog. Chem., 256:2767–2776.
Glenn et al. (1980), J. Biolog. Chem., 255:6609–6616.
Carney and Cunningham (1978), Cell, 15:1341–1349.
Carney and Cunningham (1978), Cell, 14:811–823.
Chen and Buchanan (1975), Proc. Natl. Acad. Sci. USA, 72:131–135.
CA vol. 102, 1985 Ginsberg et al.
CA vol. 90, 1979 Asstov et al.

Primary Examiner—George C. Elliott
Attorney, Agent, or Firm—Arnold, White & Durkee

[57] ABSTRACT

Thrombin is now known to mediate a number of potent biological effects on cells bearing high-affinity thrombin receptors. These effects depend, at least in part, upon receptor occupancy signals generated by thrombin's interaction with the high affinity thrombin receptor. The present inventors have formulated synthetic thrombin derivatives capable of selectively stimulating or inhibiting thrombin receptor occupancy signals. The stimulatory thrombin derivatives to bind to cell surface thrombin receptors and stimulate DNA synthesis in cells treated with non-mitogenic concentrations of alpha-thrombin or phorbol myristate acetate. Thus, these peptides, which have both a thrombin receptor binding domain and a segment of amino acids with a sequence common to a number of serine proteases, appear to generate receptor-occupancy dependent mitogenic signals. The inhibitory derivatives, which have no serine esterase conserved amino acid sequences bind to thrombin receptors without generating receptor-occupancy dependent mitogenic signals. This invention describes the peptides and methods for using them to promote cell growth and wound healing or to inhibit scar formation, tissue adhesions, and tumor metastasis and angiogenesis.

6 Claims, 6 Drawing Sheets

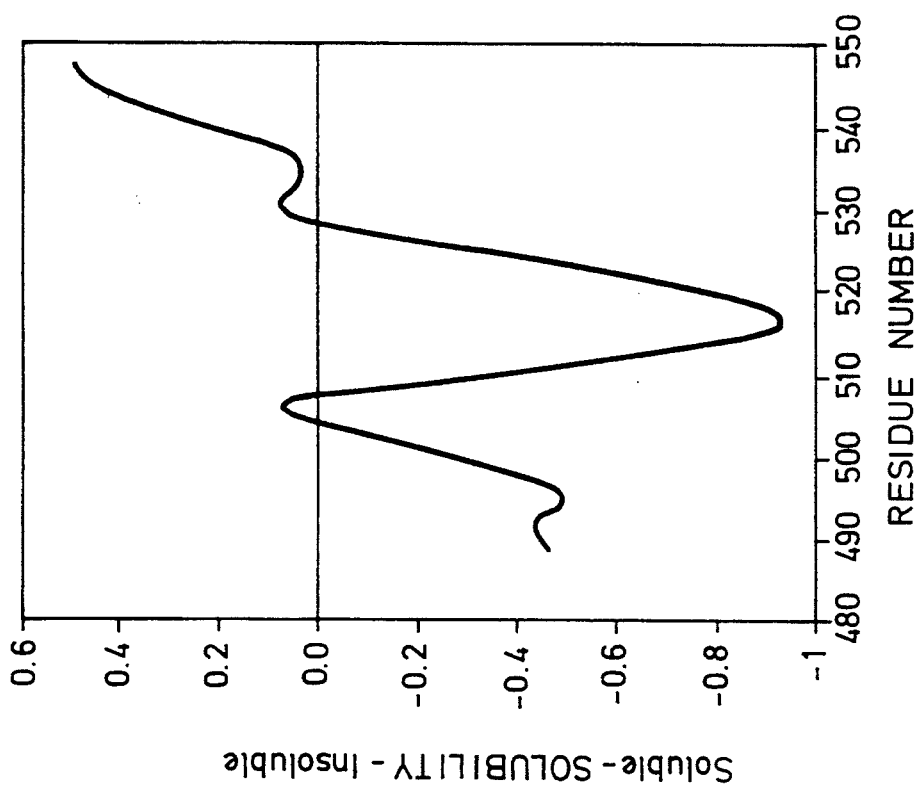
Fig. 1B  PREDICTED FREE AMINO ACID SOLUBILITY
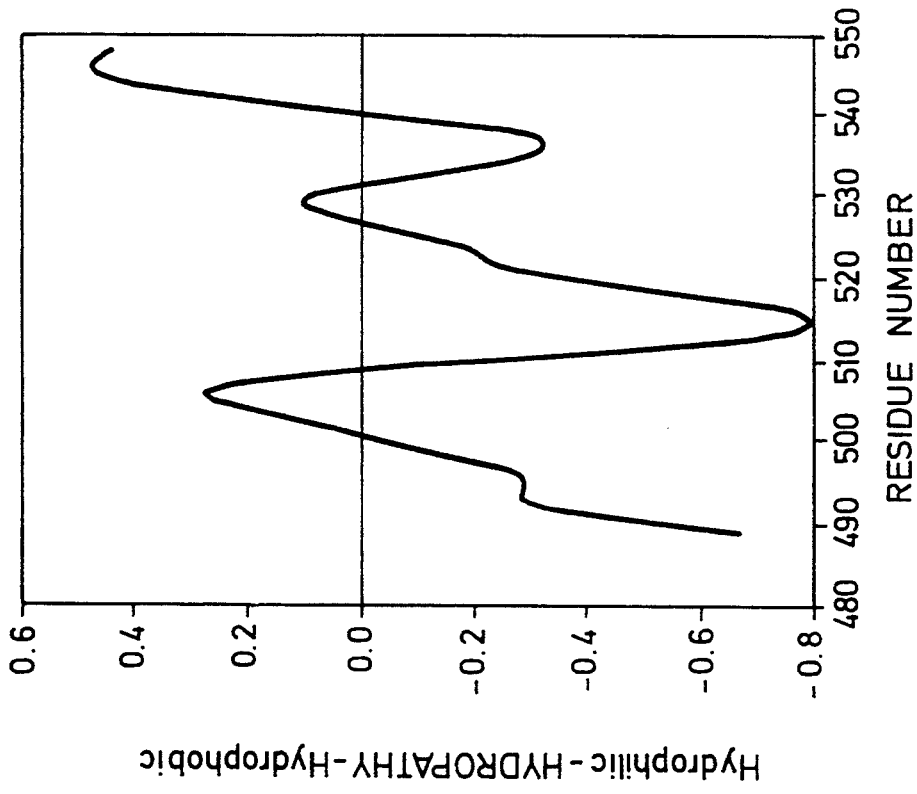
Fig. 1A  PREDICTED HYDROPATHY △ p 517-520
● p 508-530
□ p 519-530

○ Thrombin alone
● Thrombin plus p 517-520

THROMBIN DERIVED POLYPEPTIDES; COMPOSITIONS AND METHODS FOR USE

The government owns rights in the present invention pursuant to NIH Research Grant CA00805 and AM25807. FUNDING: Development of the present invention was aided in part by finding from the Department of Health and Human Services, grant nos. DHHS 5R01, AM 25807, and CA 00805. Accordingly, the U.S. Government has a paid-up license and the right in limited circumstances to require the patent owner to license others on reasonable terms as provided by the terms those grants.

BACKGROUND OF THE INVENTION

1. Field of the Invention

The present invention is directed to chemical compounds and methods useful in the regulation of thrombin receptor mediated cell stimulation. More specifically, the invention is directed to prothrombin-derived peptides and methods which employ such peptides for promoting wound healing and inhibiting scar formation, tissue adhesions, blood coagulation, tumor angiogenesis, tumor metastasis and pulmonary edema.

2. Description of the Related Art

Human alpha-thrombin appears to have growth-promoting activity for a wide variety of cells from various tissues. For example, alpha-thrombin has been shown to initiate proliferation of fibroblastic cells in culture without addition of serum or other purified growth factors, to synergize with epidermal growth factor in certain hamster fibroblasts and human endothelial cells, and to initiate cell division or DNA synthesis in mammalian lens epithelial and spleen cells. Yet, the use of thrombin as a growth factor and its potential importance to wound healing has not been widely acclaimed. In part, this may be due to the complexity of thrombin's involvement with coagulation, platelet activation, and initiation of cell proliferation as well as to the complex regulation of thrombin and thrombin-like molecules by serum protease inhibitors and by cell-released protease nexins. This complexity and high degree of physiologic regulation, however, supports the potential importance of this initiation pathway in wound healing.

Thrombin may also play a role in metastasis and angiogenesis of tumors. Generally, for a tumor to grow larger than a few millimeters in diameter, vascular endothelium must proliferate and form vesicle walls to provide circulation and nutrients to the cells inside of the tumor mass. Thrombin likely potentiates this process by virtue of its ability to induce proliferation of endothelial cells. In addition, thrombin has been shown to disrupt the normal intercellular endothelial cell contacts important in preventing cells and plasma factors from escaping or entering the microvasculature. The present hypothesis that thrombin may increase metastasis by disrupting these contacts is supported by studies demonstrating a correlation between decreased levels of anti-thrombin III (which removes thrombin and other proteases from plasma) and increased tumor metastasis.

Various studies have led the present inventors to conclude that high-affinity cell surface thrombin receptors (See Carney and Cunningham, *Cell* 15:1341, 1978) may be involved in tumor metastasis and anglogenesis. For example, studies have indicated that thrombin receptors can serve as binding sites for tissue plasminogen activator, a molecule secreted from metastatic tumor cells. Moreover, other studies demonstrate the involvement of tissue plasminogen activator in metastasis and anglogenesis. Thus, many of the effects of plasminogen activator may be mediated through its interaction with the cell surface thrombin receptor. It is therefore proposed that stimulation of the thrombin receptor serves to promote tumor metastases, while inhibition of the receptor will decrease metastatic activity.

Thrombin has also been shown to cause changes in the structure and function of cells which make up the endothelial vasculature. These studies suggest that thrombin may play a central role in the development of pulmonary edema as well as edema of other tissues. For example, thrombin has been shown to increase permeability of endothelial cell monolayers to macromolecules, to increase arterial pressure and pulmonary vascular resistance, to induce smooth muscle contraction, and to increase transcapillary fluid filtration. All of these effects may be mediated by thrombin's interaction with cell surface thrombin receptors.

A number of recent studies have attempted to elucidate the mechanisms for thrombin-mediated cell stimulation. These studies have indicated to the present inventors that initiation of cell proliferation by thrombin requires two signals. The first signal appears to be dependent upon binding of the thrombin molecule to the high affinity cell surface thrombin receptor, while the second signal results from the enzymic activity of the thrombin molecule. Thus, unlike alpha-thrombin, neither DIP-alpha-thrombin (a proteolytically inactive thrombin derivative that retains receptor-binding activity) nor gamma-thrombin (an esterolytically active, but non-binding thrombin derivative) can initiate DNA synthesis or cell division. However, simultaneous addition of these two non-mitogenic thrombin derivatives initiates a level of DNA synthesis and cell division comparable to that initiated by alpha-thrombin.

These same thrombin derivatives have been used to distinguish intracellular events stimulated by high-affinity thrombin receptor occupancy from those resulting from proteolytic cleavage. Alpha-thrombin and gamma-thrombin both stimulate $Na^+/K^+$ ATPase activity, phosphoinositol turnover, and $Ca^{2+}$ metabolism, whereas DIP-alpha-thrombin does not. Thus, these events are attributable to thrombin's enzymic activity, not to receptor occupancy. Furthermore, these signals (the release of diacylglycerol and inositol triphosphate to cause $Ca^{2+}$ mobilization) may in turn activate protein kinase C. Accordingly, it has been shown that phorbol myristate acetate (PMA), which activates protein kinase C, can substitute for enzymically active gamma-thrombin and initiate cell division in the presence of receptor saturating levels of DIP-alpha-thrombin or monoclonal antibody to the thrombin receptor. Thus, the requirements for enzymically active thrombin may indirectly relate to its activation of protein kinase C.

The precise signals generated by high-affinity interaction of thrombin with its receptor have been more difficult to define. However, it has recently been shown that DIP-alpha-thrombin stimulates a transient increase in intracellular cAMP. In contrast to ion fluxes and phosphoinositide turnover, cAMP levels are maximally stimulated by DIP-alpha-thrombin but are not stimulated by gamma-thrombin. Attempts to replace DIP-alpha-thrombin with cAMP analogs, however, have been unsuccessful. Therefore, it is possible that thrombin receptor occupancy produces a number of signals in addition to changes in cAMP levels.

One problem associated with the clinical application of thrombin directly to achieve such benefits is its susceptability to protease inhibitors by serum anti-thrombins. Such problems have heretofore prevented the use of thrombin in the clinic and has led the present inventors to identify smaller thrombin-active and thrombin antagonistic polypeptides which are not sensitive to the inhibitory effects of thrombin inhibitors.

The present invention provides for a number of smaller polypeptides which have been tailored to interact with the thrombin receptor to selectively stimulate or inhibit thrombin receptor occupancy related signals. It is believed that these polypeptides will prove to be useful in a wide variety of clinical settings where successful recovery may be influenced by thrombin receptor-mediated events.

SUMMARY OF THE INVENTION

The present invention provides a number of thrombin derivatives and methods useful for stimulating cell proliferation and promoting wound healing as well as methods useful in inhibiting wound healing, scar tissue formation, formation of tissue adhesions, and tumor metastasis and angiogenesis. The invention is based on the discovery that one may formulate polypeptide thrombin derivatives, or their physiologically functional equivalents, which selectively inhibit the interaction of thrombin with its high-affinity receptor or which mimic the stimulatory effects of thrombin.

Accordingly, the present invention, in its most general and overall scope, relates to synthetic or naturally derived polypeptide agonists and antagonists of thrombin receptor mediated events. Both of these classes of agents possess a thrombin receptor binding domain which includes a segment of the polypeptide that is capable of selectively binding to the high-affinity thrombin receptor. This segment of the polypeptide includes a sequence of amino acids homologous to a tripeptide cell binding domain of fibronectin.

In addition to the thrombin receptor binding domain, the stimulatory (agonistic) polypeptides possess a sequence of amino acids having sequences derived from the N-terminal amino acids of a dodecapeptide previously shown to be highly conserved among serine proteases. However, the inhibitory polypeptides do not include these serine esterase-conserved sequences.

The present invention is disclosed in terms of a showing that in the presence of a non-mitogenic (i.e., non-stimulatory) concentration of alpha-thrombin, gamma-thrombin, or PMA, the interaction between stimulatory polypeptides and cell surface thrombin receptors provides the cell with a signal to proliferate. However, no proliferative signal results when cell surface thrombin receptors interact with the inhibitory polypeptides. Instead, the cells become more refractory to subsequent treatment with the stimulatory polypeptides. This result is believed to occur because the inhibitory polypeptides, which are themselves incapable of generating a proliferative signal, block binding of the stimulatory polypeptides.

As indicated above, practice of the cell-stimulatory methods of the present invention requires the presence of a secondary signal, for example, in the form of non-mitogenic concentrations of alpha-thrombin, gamma-thrombin, or PMA in order to supply the cells with the low-affinity proteolytic cleavage signal. Accordingly, the invention provides for pharmaceutical compositions and methods to which these compounds have been added. However, those of skill in the art will recognize that when the invention is practiced in vivo, native alpha-thrombin endogenous to the host will typically be adequate to provide this secondary signal.

Because thrombin is involved in a number of bioregulatory effects, the present invention, which allows one to selectively promote and inhibit these effects, has a number of clinical applications. For example, the invention provides a number of polypeptides useful in promoting wound healing. For such applications, the invention provides a polypeptide derivative of thrombin (or a functional equivalent of such a derivative) which has a thrombin receptor binding domain as well as a domain with a serine esterase conserved sequence of at least 12 amino acids. The invention also provides a polypeptide compound of at least 23 L-amino acids which has both a thrombin receptor binding domain and a domain with a serine esterase conserved amino acid sequence.

In one embodiment, the invention provides for several polypeptides containing specific amino acid sequences, such as a polypeptide compound in which the thrombin receptor binding domain includes the L-amino acid sequence Arg-Gly-Asp-Ala together with the serine esterase conserved amino acid sequence, Asp-Ala-Cys-Glu-Gly-Asp-Ser-Gly-Gly-Pro-Phe-Val. In a preferred embodiment, the polypeptide compound includes the L-amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val.

The invention also provides for a pharmaceutical composition for promoting wound healing which includes of a therapeutically effective concentration of any of the compounds described above combined with a pharmaceutically acceptable excipient. Typically, such compositions include, for example, sufficient concentrations of the polypeptides to effect a stimulatory action on the thrombin receptor as demonstrated herein. Thus, such compositions should typically include sufficient concentrations to obtain levels of the polypeptides in the wound area which are shown in vitro to stimulate the receptor. When endogenous levels of a secondary signal are believed to be inadequate, compositions may be employed which further include the addition of a therapeutically effective concentration of alpha-thrombin or gamma-thrombin.

As used herein, a therapeutically effective concentration is defined as a concentration of the particular agent which provides a satisfactory increase in the rate of wound healing. Again, such concentrations are believed to correspond to levels sufficient to ellicit a stimulation of the thrombin receptor in vitro. However, it is believed that the compositions will prove most effective when the stimulatory (agonistic) polypeptides are present at a concentration of from 0.1 uM to 10 uM.

Furthermore, where alpha-thrombin or gamma-thrombin are also employed, concentrations of from 0.1 uM to 10 uM are considered effective. However, empirical methods as are known in the art may be employed for determining more precisely the proper therapeutic dose for a given composition administered in a particular manner.

In addition, methods are provided which employ thrombin agonists to promote wound healing. One such method includes applying to the wound a therapeutically effective amount of a polypeptide derivative of thrombin, or a physiologically functional equivalent thereof, which has both a thrombin receptor-binding domain and a domain having a serine esterase conserved amino acid sequence. In general, thrombin is applied in amount sufficient to achieve fibroblast stimulation and thereby stimulate tissue regeneration. In that such methods typically involve topical application to a wound, possible sytstemic toxicity is not believed to be a problem. Therefore, virtually any concentration may be employed. However, in a preferred embodiment, the wound is treated to achieve a range of approximately 1 ng/cm$^2$–10 ug/cm$^2$ of wound surface.

The invention further provides a method for promoting wound healing in which a therapeutically effective amount of alpha-thrombin (1 ng/cm$^2$–10 ug/cm$^2$ of wound surface) or gamma-thrombin (1 ng/cm$^2$–10 ug/cm$^2$ of wound surface) is applied to the wound in conjunction with the foregoing thrombin derivatives. Of course, the specific polypeptides and pharmaceutical compositions provided by the invention may also be used in promoting wound healing. It is believed that these methods will be especially beneficial to patients involved in severe accidents (particularly burn patients), to those subjected to surgical procedures and to those with poor wound healing responses, such as aged and diabetic individuals.

Additional methods are provided for using the thrombin receptor inhibitory polypeptides. For example, the invention provides methods whereby scar tissue formation can be inhibited by administering to the wound or scar tissue, a therapeutically effective amount of a polypeptide derivative of thrombin, or a physiologically functional equivalent thereof, which has a thrombin receptor binding domain but does not have a serine esterase conserved sequence. Typically, such concentrations are adequate when sufficient to inhibit thrombin receptor mediated events. In a preferred embodiment, amounts ranging from 1 ng/cm$^2$–10 ug/cm$^2$ of wound surface are considered appropriate.

In a preferred embodiment, the polypeptide derivative of thrombin has the L-amino acid sequence Arg-Gly-Asp-Ala.

In general, these methods may be used in any situation where scar formation is undesirable, such as on burn patients or those subjected to opthalmic surgery. Moreover, the methods may also be of use in preventing keloidal scar formation. It is anticipated that spraying the wound with an aerosol spray will be a particularly sterile and efficacious manner of administering the polypeptide compound to the wounds of burn patients.

The inhibitory polypeptides should also prove useful in inhibiting the formation of tissue adhesions, defined as abnormal unions between body organs by formation of fibrous tissue. It is known that fibroblast proliferation is required for formation of such adhesions. Since alpha-thrombin is known to induce fibroblast proliferation, it follows that inhibition of thrombin-mediated mitogenesis by the peptides of the present invention could reduce adhesion formation. It is believed that administration of such inhibitory polypeptides to the surface of the affected organs will prove to be especially useful following certain surgical procedures, such as thoracic surgery, where gut adhesions often lead to postoperative complications.

It is further proposed that the inhibitory peptides will prove useful in the treatment of mammals with tumors to thereby inhibit tumor metastasis or angiogenesis. This view is supported by studies demonstrating that alpha-thrombin is able to disrupt normal inter-endothelial cell contacts important in preventing metastasis, as well as studies demonstrating that alpha-thrombin can induce the proliferation of endothelial cells required for angiogenesis. Accordingly, the invention provides a method whereby mammals with such tumors receive a therapeutically effective amount of a polypeptide derivative of thrombin, or a functional equivalent thereof, which has a thrombin receptor binding domain but does not have a serine esterase conserved sequence. While exact doses would need to be determined by empiracal methods known those skilled in the art, it is estimated that an amount sufficient to achieve a concentration of from 0.1 uM to 10 uM at the site to be treated is needed. Use of a polypeptide wherein the thrombin binding domain has an L-amino acid sequence Arg-Gly-Asp-Ala is specifically provided. It is contemplated that the polypeptides will be most efficacious in this regard when administered intravenously. However, other methods of administration will also likely prove to be effective.

In a most general embodiment, the invention provides for the use of inhibitory polypeptides to inhibit cell proliferation. This method encompasses, but is not limited to, situations in which one desires to inhibit cell proliferation in vitro. Of course, the inhibitory polypeptide, having a thrombin binding domain with the specific sequence Arg-Gly-Asp-Ala, may also be used as a general inhibitor of cell proliferation.

In another general embodiment, the invention comprises methods wherein the stimulatory polypeptides are used to potentiate cell growth. A polypeptide including the sequence Ala-Gly-Tyr-Lys-Pro-Asp-Glu-Gly-Lys-Arg-Gly-Asp-Ala-Cys-Glu-Gly-Asp-Ser-Gly-Gly-Pro-phe-Val is specifically provided. This method encompasses, but is not limited to, situations wherein one wishes to potentiate cell growth in vitro. Such cell-stimulatory uses may be potentiated by further providing an effective amount of alpha-thrombin (0.1 ug/ml–10 ug/ml), gamma-thrombin (0.1 ug/ml–10 ug/ml) or phorbol myristate acetate (10 ng/ml–100 ng/ml) in conjunction with the stimulatory polypeptide.

GLOSSARY

For purposes of the present invention, a thrombin derivative is defined as any molecule with an amino acid sequence derived at least in part from that of thrombin, whether synthesized in vivo or in vitro. Accordingly, a thrombin derivative, as referred to herein, designates a polypeptide molecule which comprises fewer amino acids than thrombin.

A physiologically functional equivalent of a thrombin derivative encompasses molecules which differ from thrombin derivatives in particulars which do not affect the function of the thrombin receptor binding domain or the serine esterase conserved amino acid sequence. Such particulars may include, but are not limited to, conservative amino acid substitutions and modifications, for example, amidation of the carboxyl terminus, acetylation of the amino terminus, conjugation of the polypeptide to a physiologically inert carrier molecule, or sequence alterations in accordance with the serine esterase conserved sequences.

A thrombin receptor binding domain is defined as a polypeptide sequence which directly binds to the thrombin receptor and/or competitively inhibits binding between high-affinity thrombin receptors and alpha-thrombin.

A domain having a serine esterase conserved sequence comprises a polypeptide sequence containing at least 4–12 of the N-terminal amino acids of the dodecapeptide previously shown to be highly conserved among serine proteases (Asp-$X_1$-Cys-$X_2$-Gly-Asp-Ser-Gly-Gly-Pro-$X_3$-Val); wherein $X_1$ is either Ala or Ser; $X_2$ is either Glu or Gln; and $X_3$ is either Phe, Met, Leu, His, or Val).

A stimulatory polypeptide is defined as a polypeptide derivative of thrombin, or a physiologically functional equivalent thereof, having the ability to both bind to and stimulate the thrombin receptor. Therefore, the stimulatory peptides will include both a thrombin receptor binding domain and a domain with a serine esterase conserved amino acid sequence.

An inhibitory polypeptide is defined as a polypeptide derivative of thrombin, or a physiologically functional equivalent thereof, having a thrombin receptor binding domain but without a serine esterase conserved amino acid sequence.

BRIEF DESCRIPTION OF THE DRAWINGS

FIGS. 1A–1D. Computer assisted analysis of the hydropathy, solubility, and predicted secondary structure for residues 489 to 548 of human prothrombin. FIG. 1A, hydropathy profile; FIG. 1B, solubility profile; FIG. 1C, predicted tendency for flexible turn; FIG. 1D, predicted tendency for alpha-helix and beta-sheet structure.

FIGD. 2A–2C. Three-dimensional representations of X-ray crystallographic data of trypsin with the following PROTEUS computer-assisted substitutions of thrombin-specific residues: $Gly_{187}$ Lys; $Lys_{188}$ Arg; $Ser_{190}$ Ala; $Gln_{192}$ Glu; and $Val_{199}$ Phe is shown in FIG. 2A.

FIG. 4B) were treated with the indicted concentrations of p508–530 alone (O) or in combination with concentrations of alpha-thrombin which gave approximately one third of the maximal response; 2 nM for ME cells (FIG. 4A) and 4 nM for NIL cells (FIG. 4B). [$^3$H]-thymidine incorporation was determined after 24 hours as described in the description of the preferred embodiments.

DETAILED DESCRIPTION OF THE EMBODIMENTS

Thrombin, a molecule once considered important only in the context of blood coagulation, is now shown to mediate a number of potent biological effects not directly related to coagulation. Many of these effects are due, at least in part, to signals generated by the interaction between thrombin or thrombin-like molecules and the high-affinity thrombin receptors present on the surface of many cells.

Studies performed in connection with the present invention suggested that selective regulation of thrombin-mediated events might be achieved through the formulation and synthesis of polypeptides specifically designed to either mimic or inhibit such events. Development of small protease inhibitor resistant polypeptides capable of performing these functions was particularly desirable in view of the susceptibility of thrombin to proteolytic enzyme inhibitors, such as anti-thrombin.

A number of peptides based on the sequence of human prothrombin were synthesized and tested for their ability to bind to the receptor and to generate proliferative signals. The choice of peptides focused on the amino acid sequence of the region of thrombin around its active site serine. This region contains a domain (represented by residues 517–520 of human prothrombin) with a sequence homologous to the tripeptide cell binding domain of fibronectin, [Arg-Gly-Asp]. This tripeptide sequence is common to a number of proteins that may interact with cells (reviewed by Rouslahti and Peirschbacher, Cell, 44:517–518 (1985)). Moreover, it has been shown that a peptide representing 517–520 of human prothrombin (p517–520) and peptides representing 516–522 and 510–526 of human prothrombin (p516–522 and p510–526, respectively) are able to promote fibroblast attachment comparable to that induced by fibronectin-specific peptides.

The selected region also possesses a domain (represented by residues 519–530 of human prothrombin) with a high degree of homology to a number of serine esterases.

The present inventors have discovered that a synthetic peptide containing both fibronectin- and serine protease-homologous domains (residues 508 to 530 of human prothrombin) binds to thrombin receptors with high-affinity and substitutes for DIP-alpha-thrombin as an initiator of receptor occupancy-related mitogenic signals. In contrast, a synthetic peptide containing only the fibronectin-homologous domain (p517–520) binds to the thrombin receptor without inducing mitogenesis. An intermediate peptide (p519–530) retains the ability to mediate mitogenesis but to a much lesser degree than p508–530.

EXAMPLE 1

Figure 1D:
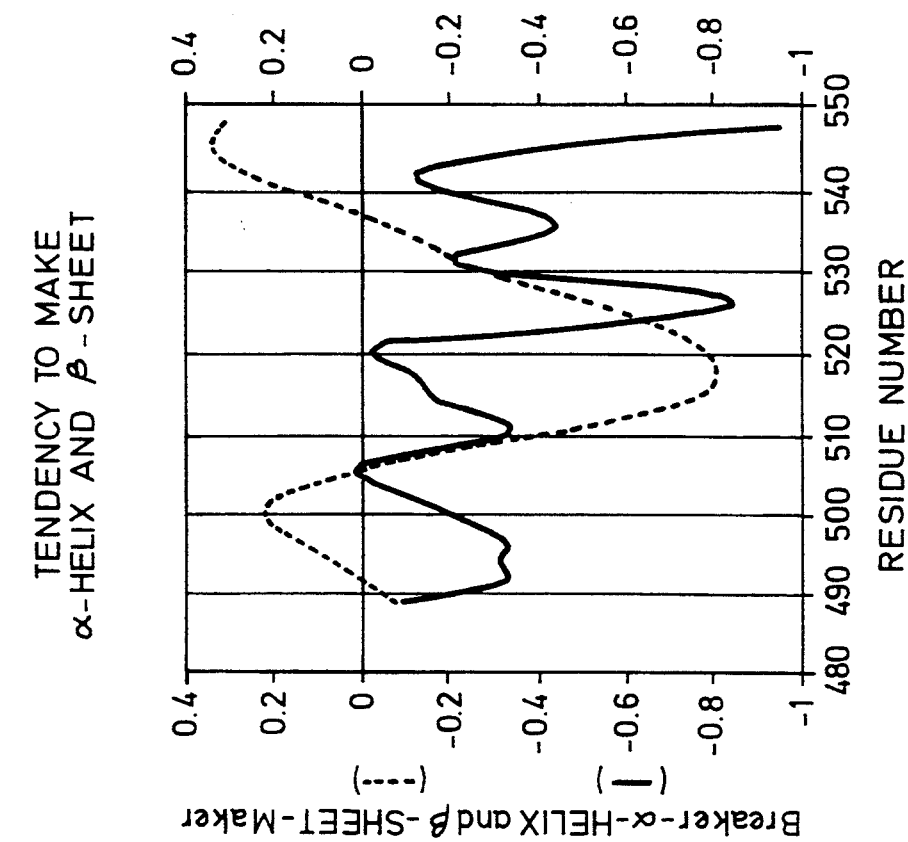
Figure 1C:
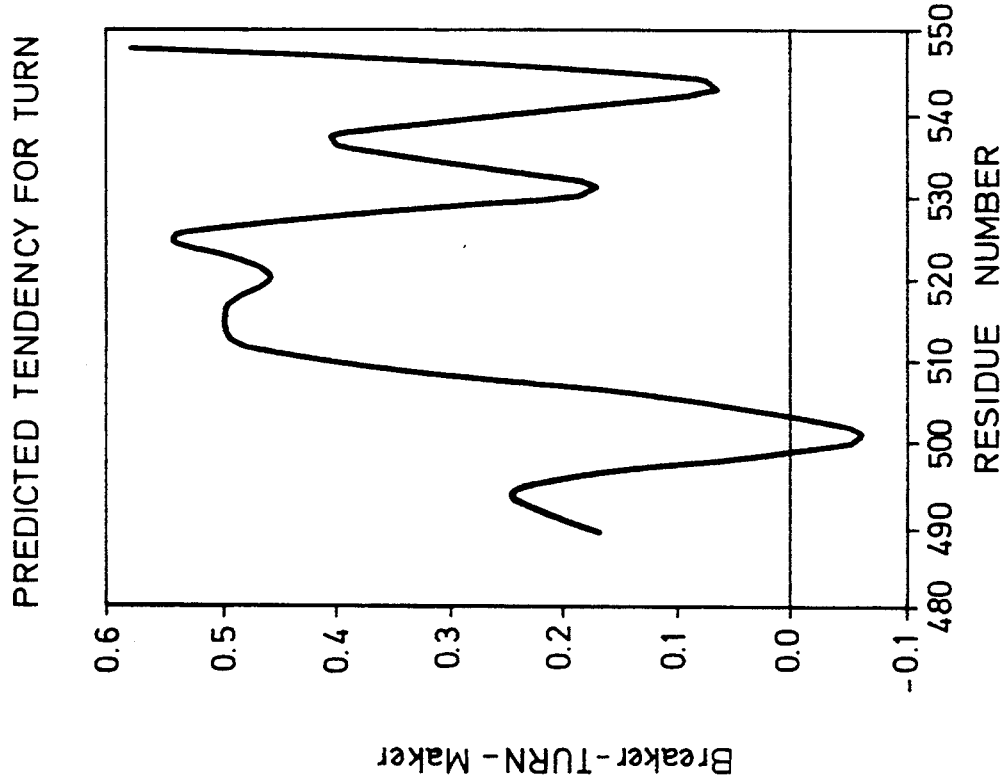

Selection of Domains of Human Alpha-Thrombin Involved in Binding of Thrombin to Its High Affinity Receptor To help select peptide sequences that might be involved in receptor binding, computer analysis was used to predict the overall hydropathy, solubility, and secondary structural features for the 60 amino acid residues around the active site serine of alpha-thrombin based on the sequence of human prothrombin (Degen et al., *Biochem.*, 2:2087–2097 (1983)). As shown in FIGS. 1A and 1B, this region appears to be highly hydrophilic and soluble, especially near the region that is homologous to fibronectin's cell attachment domain, residues 517 to 520. Analysis of secondary structural features indicated that the region of thrombin from residues 511 to 526 has a strong tendency for being a flexible turn region with very little tendency towards either alpha-helical or beta-sheet structures (FIGS. 1C and 1D). Taken together, the various computer-assisted analyses strongly suggest that this region of thrombin should be externally accessible and, therefore, available for interaction with the thrombin cell surface receptor. Moreover, the region of thrombin homologous to the cell attachment domain of fibronectin is located at or very near the middle of this hydrophilic flexible turn of thrombin.

Figure 2B:
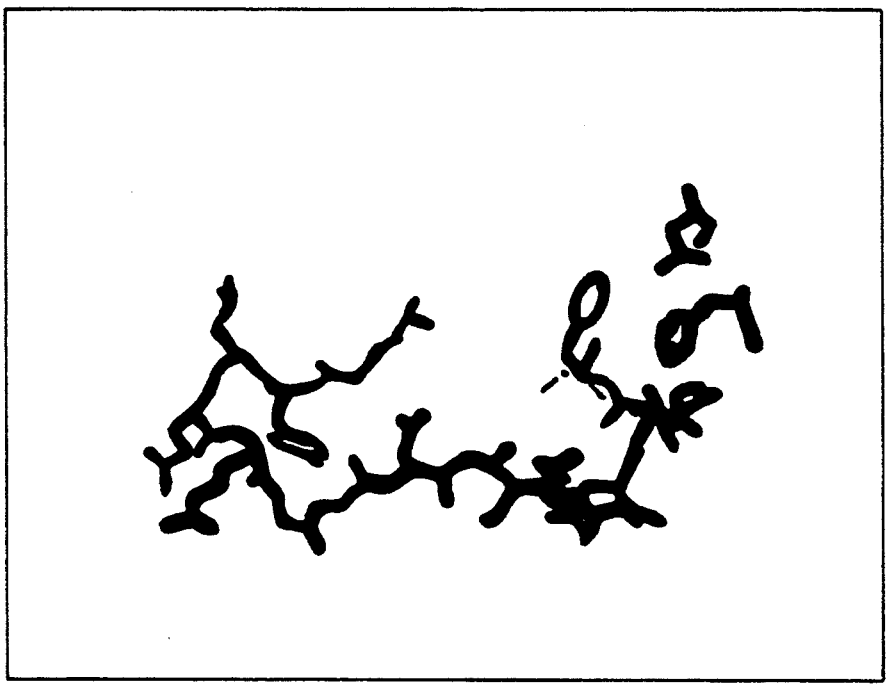
FIG. 2B and 2C show only the three active site residues ($His_{57}$, $Asp_{102}$, $Ser_{195}$) and residues 183 to 200 of trypsin that are located in the homologous region as thrombin's residues 510 to 530. These peptides are oriented in the same position as in the rotated model in FIG. 2A.
Figure 2A:
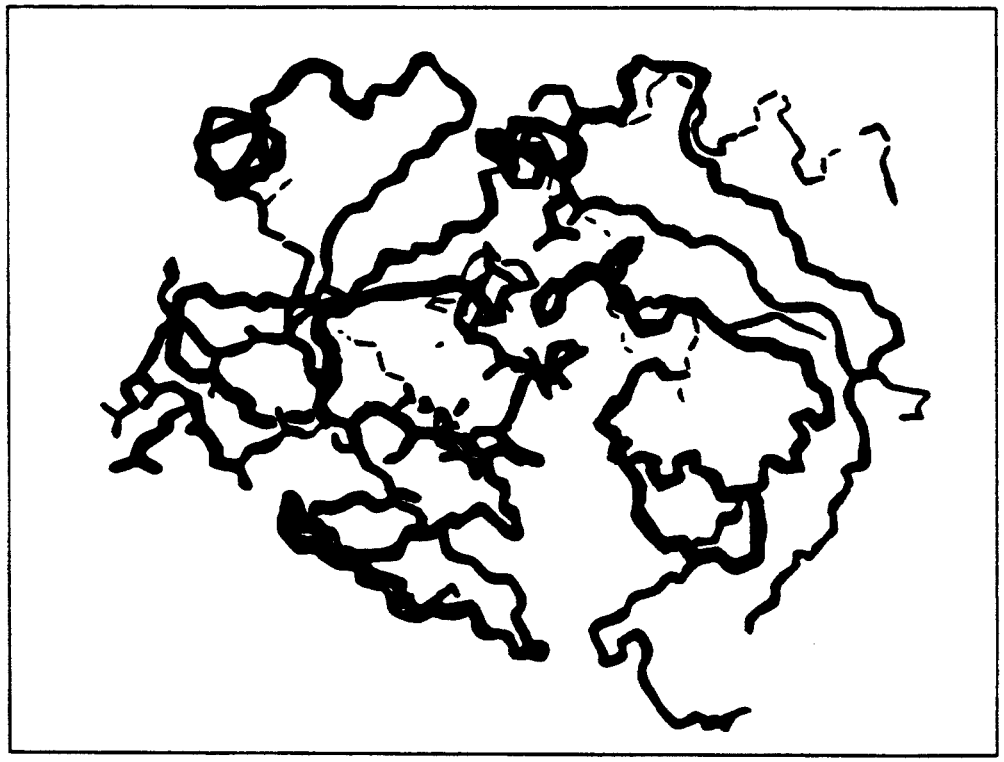
Figure 2C:
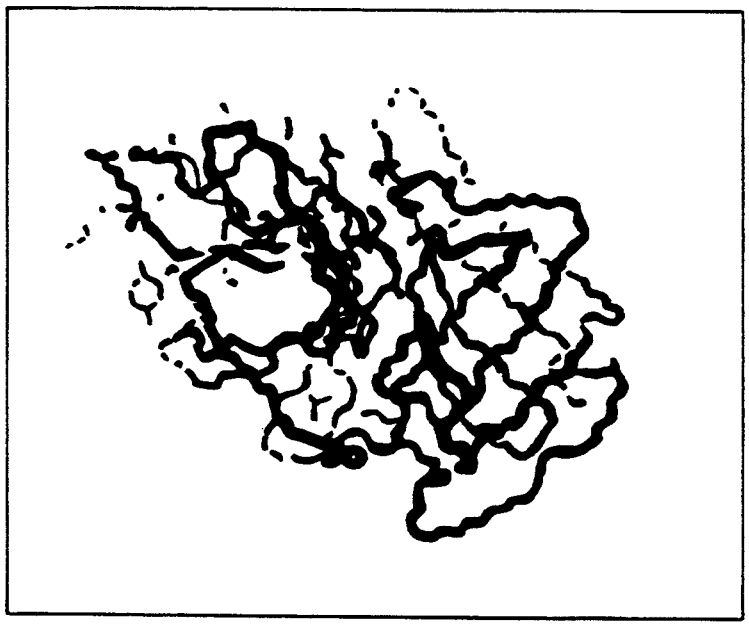

Using the three dimensional x-ray crystallographic data for trypsin (Marquart et al., *Acta. Crystallogr.*, 39:480 (1983)), and making appropriate amino acid substitutions to reflect the thrombin sequence around the active-site serine portion of trypsin, computer graphic analysis predicted that residues 510 to 530 of thrombin are located along the edge of the pocket that leads to the active site cleft (FIG. 2). In agreement with the predictions of secondary structure discussed above, amino acid residues 517 to 520 of thrombin are located at the outer most corner of this region of the proposed trypsin/thrombin structure. Thus, it appeared reasonable that this region of thrombin could be involved in binding to its receptor.

EXAMPLE 2

Synthesis of Peptides

Peptides were synthesized by the solid-phase method (Erickson and Merrifield, *The Proteins*, 2:255–257, (1976)) using automatic instrumentation (Applied Biosystems Peptide Synthesizer Model 430A) and purified by HPLC (Beckman) on a C-18 column eluted with a linear acetonitrile gradient containing 0.5% (v/v) TFA (trifluoroacetic acid).

EXAMPLE 3

Demonstration that the Thrombin Derivatives Selectively Bind to the High-Affinity Thrombin Receptor This example demonstrates that the peptides of the present invention are able to selectively bind to the high-affinity thrombin receptors present on the surfaces of many cell types. In the present embodiment, this activity was demonstrated by showing that the peptides of the present invention competitively inhibited binding of [$^{125}$I]-alpha-thrombin to thrombin receptors present on two strains of cultured fibroblasts. Accordingly, the specific techniques described below represent the best mode for demonstrating this activity known to the inventors at the present time.

a. Culture of Fibroblasts Having High-Affinity Thrombin Receptors

As stated above, fibroblasts derived from two sources were used to demonstrate binding of the peptides of the present invention to high-affinity thrombin receptors. These cell lines were prepared as follows:

Primary cultures of fibroblasts were prepared from 9- to 13-day old embryos of NIH-swiss outbred mice as described by Carney and Cunningham, *Cell*, 15:1341–1349, (1978). NIL cells, an established strain of hamster fibroblasts, were maintained as stock cultures and subcultured every four days. All cells were grown in Dulbecco-Vogt modified Eagle's (DV) medium supplemented with 10% (v/v) bovine calf serum (CS), in a humidified atmosphere of 5% $CO_2$ in air at 37° C.

Quiescent cultures were prepared by subculturing stock cells from 100 mm dishes, using 0.05% (w/v) trypsin and 0.02% EDTA (w/v) in phosphate-buffered saline (PBS) and plating them in 24-well culture plates in DV medium supplemented with 10% (v/v) CS at $6 \times 10^4$ cells/cm$^2$. After allowing the cells to attach overnight, the medium was removed and the cells were rinsed with DV medium containing no serum. The cells were incubated in this serum-free medium for 48 hours before the indicated experiments. This procedure has been shown to provide nonproliferating populations of mouse and NIL cells that are 90–95% arrested at the $G_1/G_0$ cell cycle interface.

b. Assay for Measurement of Specific Binding of Thrombin and Thrombin Derivatives to the Cell Surface Thrombin Receptor As stated above, in the present embodiment, thrombin receptor specific binding activity of the thrombin derivatives was measured as a function of their ability to competitively inhibit binding between native [$^{125}$I]-thrombin and the thrombin receptor. Specific techniques whereby the competitive binding studies were performed are set out below.

Human alpha-thrombin was iodinated in the presence of benzamidine (an active-site competitive inhibitor), lactoperoxidase, and Na[$^{125}$I]. After gel filtration and dialysis, the [$^{125}$I]-alpha-thrombin had a specific activity of 1 to $3 \times 10^{-7}$ CPM/ug and co-migrated with unlabeled alpha-thrombin as a single band on sodium dodecyl sulfate (SDS) polyacrylamide gels. These iodinated preparations retained approximately 80% of their fibrinogen clotting activity.

The ability of the synthetic peptides to compete for specific [$^{125}$I]-alpha-thrombin binding to fibroblasts was measured on nonproliferating, mitogenically responsive cultures in 24 well plates (Falcon) at a cell density of approximately $5 \times 10^4$ cells/cm$^2$ as previously described (Carney and Cunningham, *Cell*, 15:1341–1349 (1978)). The medium on the cells was changed to binding medium (serum-free DV medium containing 0.5% (w/v) bovine serum albumin buffered with 15 mM HEPES at pH 7.0). The cells were equilibrated at 23° C. for 30 minutes, and the medium was changed to binding medium containing [$^{125}$I]-alpha-thrombin (10 ng/ml) with the indicated concentrations of the peptides. After 2 hours at 23° C., the assay was terminated by quickly rinsing the cells four times with ice-cold PBS. The cells were dissolved in 1 ml of 0.5 N NaOH and the total radioactivity was measured using a Beckman gamma counter. Nonspecific binding was measured as the radioactivity bound to cultures after incubation in binding medium containing a 100-fold excess of unlabeled alpha-thrombin. Specific binding was calculated by subtracting nonspecific binding from total radioactivity bound to cultures.

c. Thrombin Binding Activity of Selected Thrombin Derivatives

In order to demonstrate the thrombin receptor binding activity of the polypeptides of the present invention, the peptides synthesized as described in Example 1 were tested for thrombin receptor activity using the assay system described immediately above.

Figure 3:
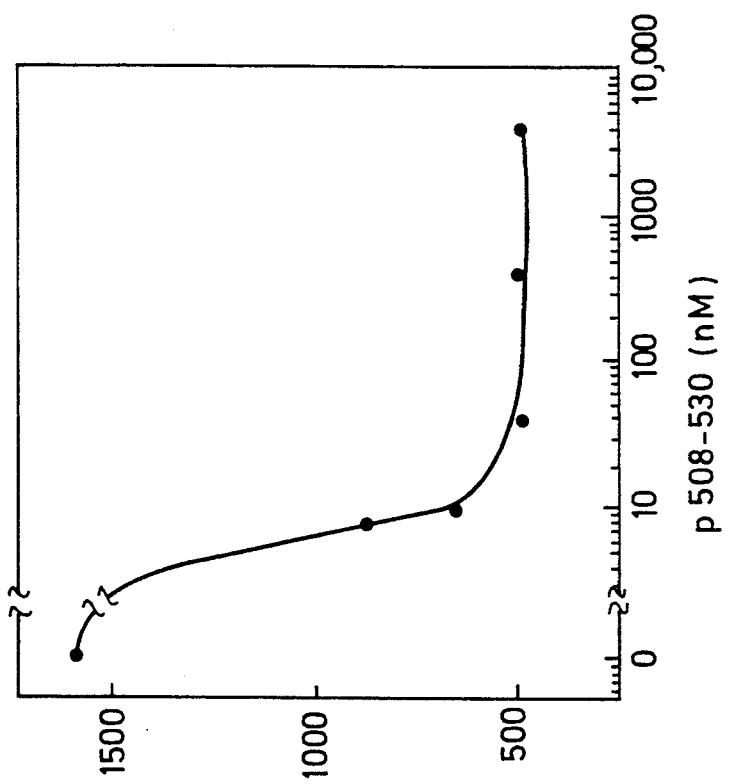
FIG. 3. Inhibition of [$^{125}$I]-alpha-thrombin binding to mouse embryo (ME) cells by synthetic peptide p508–530. Specific binding of 0.3 nM [$^{125}$I]-alpha-thrombin to ME cells in the presence of the indicated concentration of peptide was measured as described in the description of the preferred embodiments.

More specifically, in order to demonstrate that p508-530 bound to thrombin receptors, confluent cultures of ME cells were incubated with 0.3 nM [$^{125}$I]-alpha-thrombin and concentrations of p508-530 ranging from 8 to 4000 nM for 90 minutes at 23° C. As shown in FIG. 3, p508-530 competed for 30% to 70% of the specific binding of [$^{125}$I]-alpha-thrombin to ME cells. Scatchard analysis of the direct binding of [$^{125}$I]-labeled p508-530 indicated a $K_D$ of approximately $6 \times 10^{-8}$ M (data not shown). In addition, the specific binding of [$^{125}$I]-p508-530 to ME cells could be displaced by both excess p508-530 or excess human alpha-thrombin. Thus, it appears that the competition of p508-530 for [$^{125}$I]-alpha-thrombin binding represents the binding of p508-530 to the same sites as alpha-thrombin, but with an affinity approximately one order of magnitude lower.

Furthermore, in order to show that the binding and mitogenic activity of p508-530 was specific, two synthetic peptides with physical properties similar to p508-530 but no sequence homology to human alpha-thrombin were tested for their binding properties. Both of these peptides [one with 12 amino acids (33% hydrophobic residues and a net charge of $-3$) and a second with 18 amino acids (39% hydrophobic residues and a net charge of 0)] inhibited binding of [$^{125}$I]-alpha-thrombin less than 5% at concentrations up to 5 uM.

To further identify regions of thrombin involved in high-affinity binding and generation of mitogenic signals, two peptides representing specific domains within p508-530 were tested. The first peptide represented residues 519 to 530 of the B-chain region of human prothrombin, a region of thrombin that is highly conserved among serine proteases. The second peptide represented residues 517 to 520 of prothrombin, a region of thrombin homologous to the fibronectin cell binding domain.

Both of these peptides were able to compete for 30% to 50% of the binding of [$^{125}$I]-alpha-thrombin to ME cells, but both required higher concentrations than was required with the initial peptide p508-530 (Table 1). For example, 30% inhibition of [$^{125}$I]-alpha-thrombin binding required 33- to 50-fold higher concentrations of p519-530 and p517-520 than p508-530, respectively. Thus, both of these peptides appear to interact with thrombin receptors, but at a lower affinity than p508-530. Because p517-520 is homologous to the fibronectin cell binding domain, a peptide having the sequence Arg-Gly-Ala-Ser (the sequence of the fibronectin specific peptide) was also tested for its ability to compete for [$^{125}$I]-alpha-thrombin binding. At a concentration of 1.3 uM, this peptide did not compete with [$^{125}$I]-alpha-thrombin for binding. Thus, the receptor for alpha-thrombin is not the same membrane protein that specifically interacts with fibronectin and causes the apparent growth promoting action of fibronectin. In addition, these results demonstrate the requirement for alanine within the thrombin receptor binding domain, since substitution of alanine with serine eliminated the ability of the synthetic peptide to compete for alpha-thrombin binding.

TABLE 1

Comparison of Peptide Competition for [$^{125}$I]-Alpha-Thrombin Binding to ME Cells.

| Peptide | Amino Acid Sequence | Concentration Required for 30% Inhibition | Maximal % Inhibition (and Conc.) |
|---|---|---|---|
| p508-530 | AGYKPDEG— —KRGDACE— —GDSGGPFV | 6 nM | 78% (40 nM) |
| p519-530 | DACEGD— —SGGPFV | 200 nM | 51% (800 nM) |
| p517-520 | RGDA | 300 nM | 50% (2.7 uM) |

Various concentrations of peptides and [$^{125}$I]-alpha-thrombin (1 nM) were incubated with quiescent ME cells for 90 minutes at 23° C. Specific binding of [$^{125}$I]-alpha-thrombin was defined as described in Example 3.

EXAMPLE 4

Stimulation of DNA Synthesis by Selected Thrombin Derivatives

This example demonstrates that binding between stimulatory (agonistic) polypeptides and thrombin receptors generates a receptor occupancy signal which induces DNA synthesis and cell division. In the present embodiment, DNA synthesis and cell proliferation was measured as a function of [$^3$H] thymidine uptake by cultured fibroblasts exposed to selected polypeptides in the presence of non-mitogenic concentrations of alpha-thrombin or PMA. Although the in vitro techniques described below represent the best mode for demonstrating the stimulatory activity of the selected polypeptides, those skilled in the art will appreciate that the principles demonstrated in the in vitro system described immediately below are also applicable in vivo.

a. Techniques for Measuring DNA Synthesis

The effects of the synthetic peptides on DNA synthesis were determined by measuring the incorporation of methyl-[$^3$H]-thymidine (TdR, ICN Pharmaceuticals, Irvine, Ca.) during a 2 hour incubation generally from 22 hours after addition of peptides and/or thrombin (Stiernberg et al., J. Cell Physiol., 120:209-285 (1984)). After incubation, the cells were extracted and rinsed with ice-cold 10% (w/v) trichloroacetic acid (TCA). The acid precipitable material was dissolved overnight in 0.5 ml 0.5 N KOH at 23° C. HCl (1 N), 0.25 ml, was added and the solution was counted in 10 ml of RediSolv-HPb (Beckman Instruments, Houston, Tex.) scintillation fluid.

b. Mitogenic Activity of Selected Thrombin Derivatives

Each of the thrombin derivatives synthesized was tested for mitogenic activity as were the two non-thrombin peptides described in Example 3(c). The results of these experiments are described below.

Figure 4:
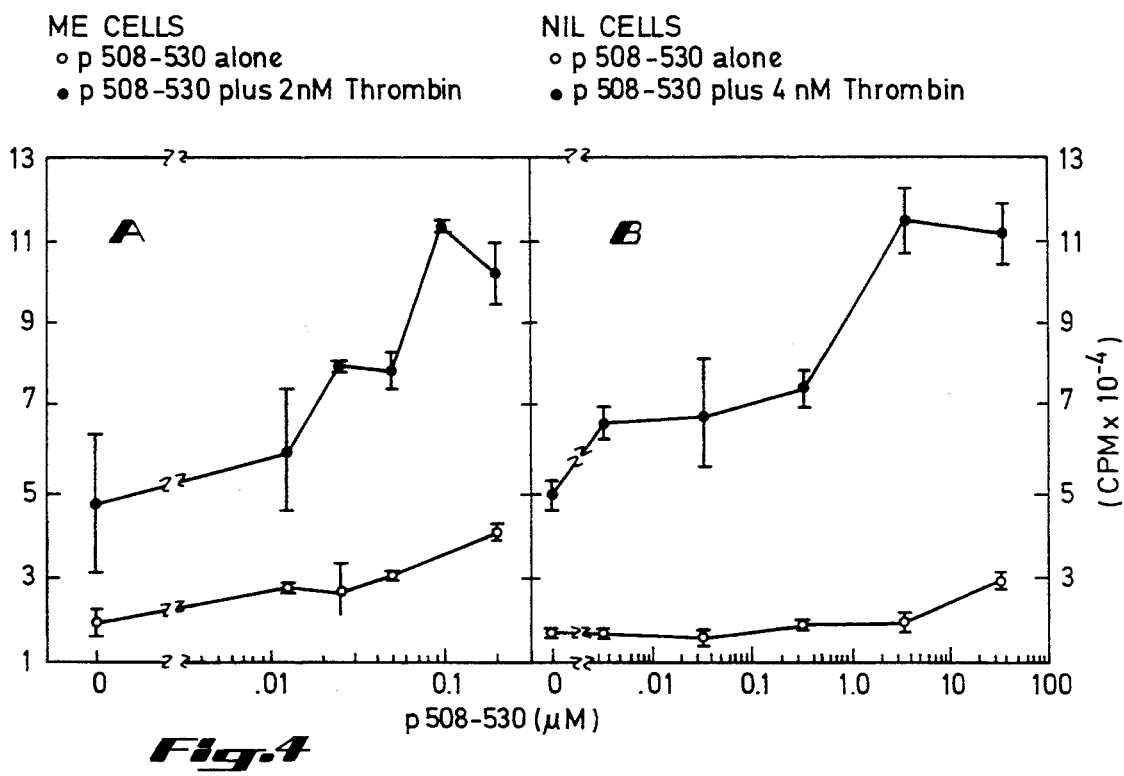
FIG. 4 Effect of p508–530 on [$^3$H]-thymidine incorporation alone or in combination with low concentrations of alpha-thrombin. Quiescent serum-free cultures of ME (FIG. 4A) or NIL (a hamster fibroblast cell line.

The present inventors first tested the ability of p508-530 to stimulate DNA synthesis in non-proliferating cultures of ME or NIL cells. As shown in FIG. 4, p508-530, by itself, was not sufficient to stimulate [$^3$H]-thymidine incorporation into DNA. However, in combination with 2 nM alpha-thrombin, 0.1 uM p508-530 stimulated a 6- or greater than 2-fold increase in incorporation of [$^3$H]-thymidine into DNA in ME cells when compared to parallel cultures left untreated or treated with alpha-thrombin alone, respectively (FIG. 4A). A similar mitogenic stimulation was also observed in NIL hamster cells, although it required a slightly higher concentration of thrombin and peptides (FIG. 4B). The responses in both cell types were equivalent to the mitogenic response stimulated by a maximally effective concentration of alpha-thrombin (10 nM). It is noteworthy that for ME cells, stimulation by p508-530 was observed between 12.5 nM and 100 nM (FIG. 4A), concentrations that correspond closely with those required to inhibit [$^{125}$I]-alpha-thrombin binding to ME cells (FIG. 3). With NIL cells, a similar correlation was observed between the mitogenic concentrations of p508-530 and the concentrations required to inhibit thrombin binding, although at higher levels than required with ME cells.

Figure 5:
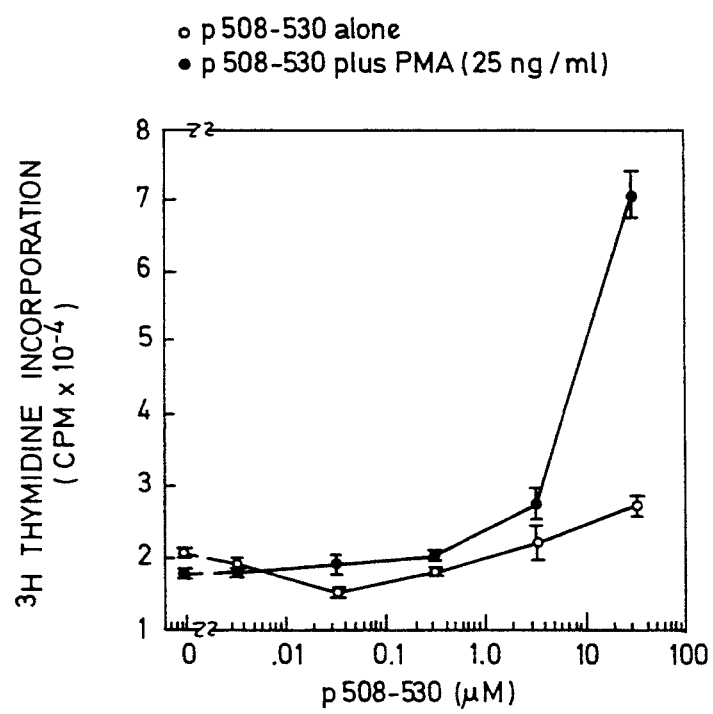
FIG. 5 Effect of p508–530 on [$^3$H]-thymidine incorporation in combination with PMA. Quiescent cultures of NIL cells were incubated with p508–530 alone (O) or in combination with 25 ng/ml PMA. [$^3$H]-thymidine incorporation was determined as described in the description of the preferred embodiments.

Although these results suggest that p508-530 generates mitogenic signals through its interaction with high-affinity thrombin receptors, it was possible that the peptide merely increased the effective concentration of alpha-thrombin. Recently, phorbol myristate acetate (PMA) has been shown to mimic the effects of gamma-thrombin and stimulate DNA synthesis and cell proliferation in combination with DIP-alpha-thrombin or with monoclonal antibodies to the thrombin receptor. It was predicted, therefore, that if p508-530 was generating a receptor occupancy-related signal, its addition to cells in combination with PMA should stimulate mitogenesis. As shown in FIG. 5, in the presence of 25 ng/ml PMA (which is a non-mitogenic amount), p508-530 stimulated a 3.5-fold increase in DNA synthesis over controls. This stimulation occurred at approximately the same concentration of peptide as that required to stimulate DNA synthesis in the presence of low concentrations of alpha-thrombin. Since active thrombin was not present in these experiments, it would appear that p508-530 itself generates a mitogenic signal that mimics the effect of DIP- or alpha-thrombin binding to high-affinity thrombin receptors.

In order to ensure that the stimulation of DNA synthesis by p508-530 was mediated by virtue of its ability to interact with the high-affinity thrombin receptor, the synthetic, non-thrombin, non-receptor binding polypeptides described in Example 3(c) were tested for mitogenic activity. Neither of these peptides generated a mitogenic response in the presence of 1 nM alpha-thrombin. Thus, neither the binding activity nor the mitogenic activity of p508-530 is due to non-specific interaction of the polypeptide with the cells.

Figure 6:
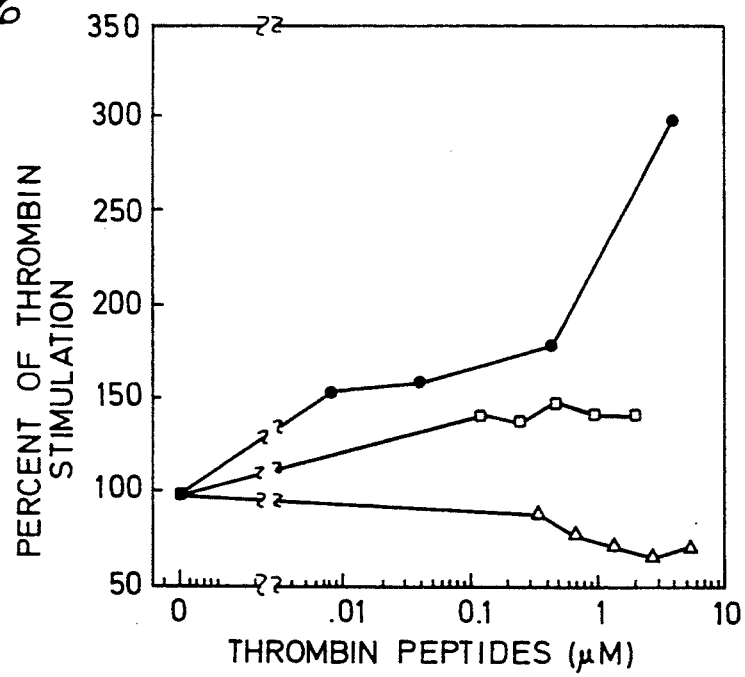
FIG. 6. Comparison between effects of peptides on thrombin-stimulated thymidine incorporation. Quiescent cultures of NIL cells were incubated with increasing concentrations of p508–530, p519–530, or p517–520 in the presence of 1 nM alpha-thrombin (a marginally mitogenic concentration). Data are expressed for each concentration as a percentage of the effect of alpha-thrombin alone.

The inventors then tested the mitogenic activity of the smaller thrombin derivatives, p519-530 and p517-520. As indicated in Example 3(c) above, both of these peptides bind to the high-affinity thrombin receptor. In these experiments, increasing concentrations of p519-530 and p517-520 were added to quiescent NIL cells in the presence of 2 and 4 nM alpha-thrombin. As shown in FIG. 6, p519 enhanced DNA synthesis over a range of concentrations while p517-520 did not. In fact, p517-520 actually inhibited DNA synthesis.

EXAMPLE 5

Inhibition of Thrombin-Receptor Mediated Mitogenesis by p517-520

The observation that p517-520 inhibits alpha-thrombin stimulated mitogenesis was somewhat startling in view of previous studies demonstrating that mitogenic and transmembrane signaling effects of thrombin were not inhibited by DIP-alpha-thrombin, a thrombin derivative which competes for active alpha-thrombin binding. Thus, the inventors realized that p517-520, which is able to compete with native alpha-thrombin for binding to high-affinity cell surface thrombin receptors, but is unable to generate the mitogenic receptor occupancy signal, has properties not previously known in the art.

Figure 7:
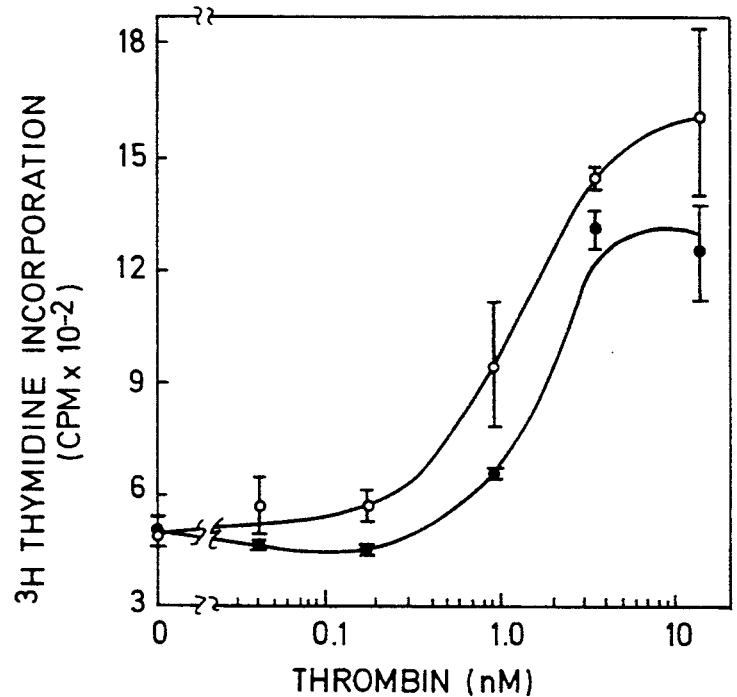
FIG. 7. Effect of p517–520 on thrombin stimulation of [$^3$H]-thymidine incorporation. Quiescent cultures of ME cells were incubated with increasing concentrations of alpha-thrombin alone, or in combination with 625 nM p517–520. [$^3$H]-thymidine incorporation was determined as described in the description of the preferred embodiments.

In order to explain the mechanism by which p517-520 was able to inhibit thrombin-mediated mitogenesis, the inventors measured the ability of increasing concentrations of alpha-thrombin to stimulate DNA synthesis in cultures to which a constant concentration (625 nM) of p517-520 had been added (FIG. 7). These experiments showed that p517-520 significantly shifted the dose-response curve of the cells to alpha-thrombin. For example, at two concentrations of alpha-thrombin, 0.8 and 13.0 nM, DNA synthesis was inhibited by approximately 75% and 35%, respectively. Thus, the inhibition of alpha-thrombin stimulation by p517-520 appears to require a 500-1000 fold molar excess of the peptide. This finding is consistent with the observation that p517-520 has a lower competitive binding affinity for thrombin receptors on ME cells than does p508-530.

The identification of p517-520 as the high-affinity binding domain of thrombin has several implications as to the mechanism of thrombin mitogenesis. Previous studies have demonstrated proteolytic cleavage and disappearance of a molecule on the surface of chick embryo cells treated with thrombin. Cross-linking studies with active or inactive thrombin have also identified two differently sized receptor molecules or substrates. The present results show that the high-affinity binding domain of thrombin is very close to the active-site cleft; thus, it should be possible for thrombin to cleave its receptor. Preliminary data from affinity purification of the thrombin receptor supports the hypothesis that the receptor itself is proteolytically cleaved by active thrombin. It is possible that thrombin receptor occupancy may stimulate an alteration in receptor conformation necessary for the cleavage event. The present results suggest that peptides p508-530, p519-530 or alpha-thrombin itself are capable of binding to the thrombin receptor in a manner which induces such confirmational changes. In contrast, p517-520 appears to be capable only of binding to the receptor. Thus, p517-520 selectively inhibits thrombin receptor-mediated events by virtue of its ability to selectively interact with thrombin receptors in a manner which provides the cell with a null signal.

EXAMPLE 6

Use of Stimulatory Peptides to Potentiate Cell Growth In Vitro

A number of experimental and diagnostic procedures require cells grown in vitro. Because the stimulatory peptides enhance proliferation of fibroblastic cells bearing high-affinity thrombin receptors, the incorporation of such stimulatory molecules into the culture medium will provide an effective means of potentiating cell growth. In addition, because thrombin stimulates proliferation of other cells, including endothelial cells, these peptides may be effective in promoting growth of a number of types of cells. Use of the synthetic polypeptides as growth supplements has a number of advantages. It is much less expensive to synthesize the polypeptides than its is to purify naturally occurring thrombin. Furthermore, unlike naturally occurring thrombin, the polypeptides are relatively resistant to inhibition by serum protease inhibitors.

Numerous methods for preparing cells for culture are known to those skilled in the art. One such method, described by Carney et al. (*J. Cell. Physiol.*, 95:13-22, 1978, incorporated herein by reference), is believed to be particularly well suited to the practice of this aspect of the invention.

As will be appreciated by those of skill in the art, the stimulatory polypeptides of the present invention may be employed together with any suitable cell culture medium to achieve the advantages of their cell-stimulation effects. For example, the present inventors have found a mixture of Dulbecco-Vogt modified Eagle's medium and Ham's F12 medium to be a particularly appropriate base medium. To practice the invention, one adds 0.1 ug/ml–10 ug/ml of the stimulatory peptide Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val to the culture medium. The cells are then incubated in an appropriate humidified atmosphere, for example, one containing 5% $CO_2$ in air at 37° C. At regular intervals (3 or 4 days), the spent medium is removed from the cell culture and replaced with fresh medium formulated as described above.

EXAMPLE 7

Treatment Protocols

Due to precautions necessarily attendant to development of every new pharmaceutical, the polypeptides of the present invention have not yet been tested in a clinical setting in human subjects. However, the in vitro activity of these polypeptides in selectively promoting or inhibiting thrombin-mediated mitogenesis is believed to demonstrate the utility of the present invention in this regard. The following prophetic embodiments represent the best mode contemplated by the present inventors of carrying out the practice of the invention in various clinical settings.

a. Wound Healing

It is believed that the stimulatory polypeptides will prove to be useful in numerous clinical situations where it is desirable to potentiate wound healing. In particular, these include treatment of burn patients, those involved in severe accidents, those subjected to a variety of surgical procedures and those with poor wound healing responses, such as the aged and diabetic. Although the best mode of administering the polypeptides will depend on the particular clinical situation, it is believed that its administration in the form of an aerosol spray will prove to be particularly advantageous in a number of such settings. Methods for incorporating therapeutic agents into aerosol sprays are well known in the art. Therefore, it is considered that formulation and use of these stimulatory polypeptides in such aerosol sprays is well within the skill of the art in light of the present disclosure.

The stimulatory polypeptide may also be applied to the wound in the form of a salve or lotion. Alternatively, they may be incorporated into the material used to dress the wound. Techniques for incorporation of therapeutic agents compositions into salves, lotions and wound dressings are also well known in the art and within the skill of the art in light of the present specification.

It is believed that an effective dose of the polypeptide is approximately between 0.5 uM–50 uM. However, exact dosages would, of course, be determined empirically by experimental methods well known to those skilled in the pharmaceutical arts.

b. Use of the Inhibitory Polypeptides

1. Inhibition of Scar Formation and Formation of Tissue Adhesions

It is further believed that the inhibitory polypeptides will prove useful in a number of situations, for example, where inhibition of fibroblast proliferation is desirable. These include prevention of scar formation and tissue adhesions.

One manner in which the invention may be practiced is by incorporating the inhibitory polypeptide Arg-Gly-Asp-Ala into any vehicle suitable for application to a wound, surgical incision or surface of a body organ. These vehicles include aerosol sprays, salves and lotions appropriate for direct application to tissues as well as solutions appropriate for intravenous or subcutaneous injections. Methods for incorporating therapeutic agents into pharmaceutical vehicles such as those described above is believed to be well within the skill of the art, as are methods for applying the resultant compositions.

It is proposed that an effective dose of the polypeptide is 1 $ng/cm^2$–10 $ug/cm^2$ if the compound is applied topically. If injected, an effective dose is that dose sufficient to obtain a concentration of the polypeptides of from 0.1 uM to 10 uM, at the site where needed. However, exact doses, of course, should be determined by accepted pharmaceutical methods known to those skilled in the pharmaceutical arts.

2. Tumor Therapy

It is believed that the inhibitory polypeptides will further prove to be useful in the treatment of various tumors, particularly in preventing metastasis and anglogenesis. It is anticipated that the inhibitory polypeptides could best be administered by intravenous administration.

The inhibitory polypeptides could be given daily by continuous infusion or on alternative days, with more traditional chemotherapy being given on the intervening day. While exact doses of the inhibitory peptides would have to be determined empirically by methods known to those skilled in the art, it is estimated that an effective dose would be that amount sufficient to achieve a concentration of 0.1 uM to 10 uM at the site where needed. Of course, as with a new pharmaceutical agent of any type, clinical trials would be needed to establish levels at which unacceptable toxicity would be reached.

The present invention has been disclosed in terms of specific embodiments believed by the inventor to be the best mode for carrying out the invention. However, in light of the disclosure hereby provided, those of skill in the various arts will recognize that modifications can be made without departing from the intended scope of the invention. For example, any of these peptides may be administered by a number of methods known in the art. Furthermore, future studies are expected to result in production of thrombin derivatives with increased stimulatory or inhibitory activity. These and all other modifications and embodiments are intended to be within the scope of the claims.

What is claimed is:

1. A polypeptide consisting essentially of a thrombin receptor binding domain and a serine esterase conserved sequence wherein said polypeptide comprises 23 amino acids.

2. A polypeptide thrombin derivative consisting essentially of: Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val.

3. A polypeptide consisting of the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val.

4. A composition of matter comprising:
 a substantially purified thrombin derivative peptide or physiologically functional equivalent thereof of 23 amino acids in length wherein said peptide includes;
 (a) a thrombin receptor binding domain having the sequence Arg-Gly-Asp-Ala; and
 (b) a serine esterase conserved sequence;
 and wherein the Asp-Ala of the thrombin receptor binding domain comprise the first two amino acids of the serine esterase conserved sequence.

5. The composition of claim 4 wherein the serine esterase conserved sequence is Asp-Ala-Cys-Glu-Gly-Asp-Ser-Gly-Gly-Pro-Phe-Val.

6. The composition of claim 4 wherein the serine esterase conserved sequence comprises AspAla-Cys-Glu-Gly-Asp-Ser-Gly-Gly-Pro-Phe-Val.

* * * * *